(12) United States Patent
Lee et al.

(10) Patent No.: US 6,600,025 B1
(45) Date of Patent: Jul. 29, 2003

(54) INTERMEDIATES, PROCESS FOR PREPARING MACROLIDE ANTIBIOTIC AGENT THEREFROM

(75) Inventors: Tae Suk Lee, Kyunggi-do (KR); Chang Hyun Yoo, Kyunggi-do (KR); Kyoung Soo Kim, Kyunggi-do (KR); Hyun Suk An, Kyunggi-do (KR); Jung Young Kim, Seoul (KR); Wan Joo Kim, Seoul (KR)

(73) Assignees: Chemtech Research Incorporation (KR); Hansol Chemience Co., Ltd. (KR)

( * ) Notice: Subject to any disclaimer, the term of this patent is extended or adjusted under 35 U.S.C. 154(b) by 0 days.

(21) Appl. No.: 09/856,383

(22) PCT Filed: Nov. 24, 1999

(86) PCT No.: PCT/KR99/00708

§ 371 (c)(1),
(2), (4) Date: Sep. 6, 2001

(87) PCT Pub. No.: WO00/31099

PCT Pub. Date: Jun. 2, 2000

(30) Foreign Application Priority Data

Nov. 24, 1998 (KR) .............................. 98/50425
Nov. 16, 1999 (KR) .............................. 99/50802

(51) Int. Cl.[7] ............................ C07H 1/00; C07H 17/08
(52) U.S. Cl. .......................... 536/7.3; 536/7.2; 536/7.4; 536/18.5
(58) Field of Search .............................. 536/18.5, 7.2, 536/7.3, 7.4

(56) References Cited

U.S. PATENT DOCUMENTS 5,872,229 A * 2/1999 Liu et al. .................... 536/18.6

OTHER PUBLICATIONS

The Journal of Antibiotics (Apr. 1993), vol. 46, No. 4, pp. 647–660.
The Journal of Antibiotics (Jul. 1993), vol. 46, No. 7, pp. 1163–1167.
The Journal of Antibiotics (Feb. 1984), vol. 376, No. 2, pp. 187–189.
The Journal of Antibiotics (Mar. 1990), vol. XLIII, No. 3, pp. 286–294, 295–305.
Heterocycles, vol. 36, No. 2, 1993, pp. 243–247.
Synthetic Communications, 10(6), 1980, pp. 465–468.
Erythromycin II Des–N–methylerythromcyin and N–Methyl–C14–erythromcyin, vol. 77, Jun. 5, 1955, pp. 3104–3106.

* cited by examiner

*Primary Examiner*—Elli Peselev
(74) *Attorney, Agent, or Firm*—Anderson, Kill & Olick; Eugene Lieberstein; Michael N. Meller

(57) ABSTRACT

An erythromycin A 9-O-benzodithiol oxime intermediate represented by the following formula (III) useful for synthesis of clarthromycin and crystalline solvate thereof:

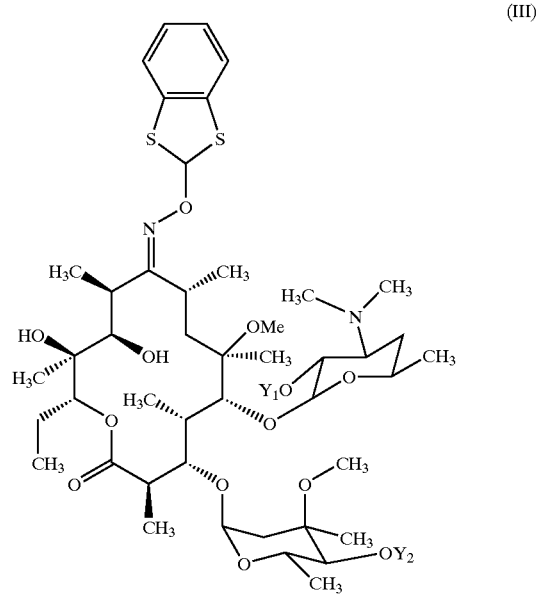

(III)

Wherein, $Y_1$ and $Y_2$ are independently a hydrogen atoms or trimethylsilyl groups. And, a process for the preparation of clarithromycin using the erythromycin A 9-O-benzodithiol oxime intermediate as described in the specification.

8 Claims, No Drawings

INTERMEDIATES, PROCESS FOR PREPARING MACROLIDE ANTIBIOTIC AGENT THEREFROM

FIELD OF THE INVENTION

The present invention relates to a novel process for the preparation of clarithromycin represented by formula (I), which has broad antimicrobial activity as a macrolide antibiotic agent, and a novel intermediate that can be used for its synthesis.

(I)

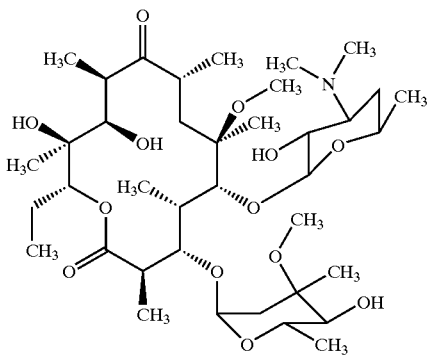

BACKGROUND OF THE PRIOR ART

To date, processes for the preparation of the above-mentioned compound of formula (I) are described in Korean Patent Publication Nos. 91-5898, 91-7572, 91-2142, 95-9367, and 96-434, Korean Laid-Open Patent Publication Nos. 90-18132 and 91-7953 as well as several literatures, for example, J. Antibiotics (Vol.46, No.4, 647(1993)), J. Antibiotics (Vol.46, No.7, 1163(1993), J. Antibiotics (Vol.37, No.2, 187(1984)), Heterocycles (Vol.36, No.2, 243(1993)), and J. Antibiotics (Vol.43, No. 3, 286(1990)). These processes may be summarized in the following three ways:

<Process 1>

This process comprises protecting 3'-N,N-dimethylamino group and 2'-OH group of erythromycin 9-oxime derivative, wherein an OH group is protected, with a carbobenzyloxy (Cbz) group and then methylating the hydroxyl group at the 6 position of said compound (see Korean Patent Publication Nos. 91-5898 and 91-7572). However, this process has the disadvantages that an excess Cbz-Cl that is relatively expensive should be used, and even though the deprotection is carried out by the hydrogen reaction, this reaction is not completed on account of the catalytic poison. Further, since the methyl group of 3'-N,N-dimetylamino group of said compound has to be regenerated by methylation in the final step of the process, it has the additional disadvantages that it is difficult to perform the process, and the process is lengthy. This process may be represented by the following scheme:

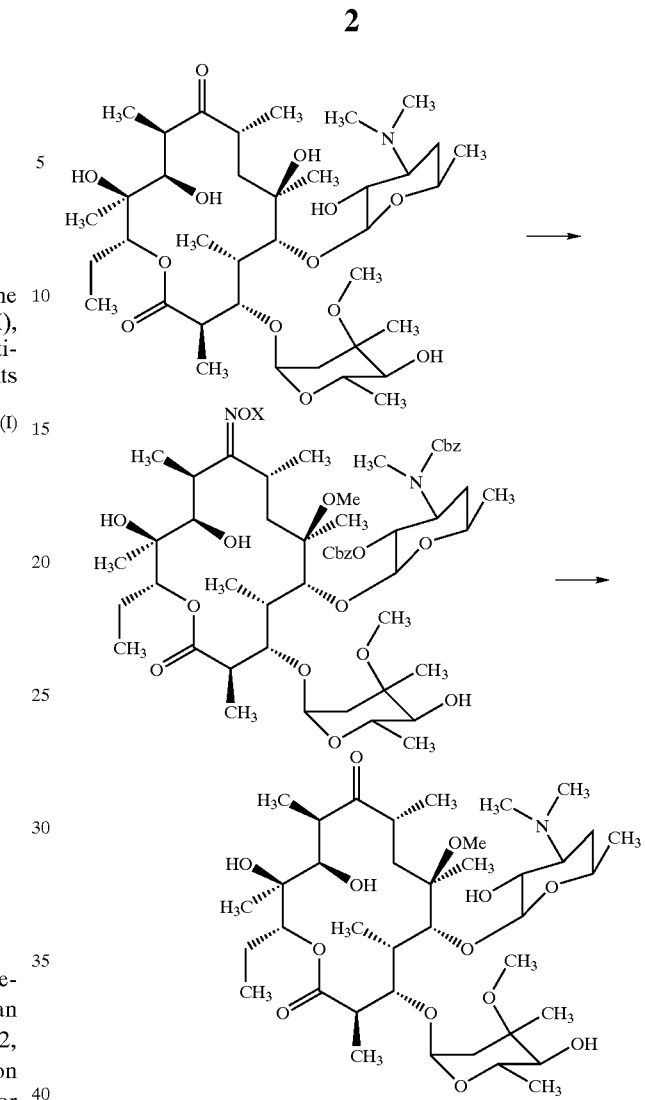

<Process 2>

This process comprises protecting 3'-N,N-dimethylamino group of erythromycin 9-oxime derivative, wherein an OH group is protected, with a quaternary salt of an identical group (for example, benzyl group)(see Korean Patent Publication No.91-2142). Since the deprotection in this process is also carried out by using hydrogen as in process 1, it has the disadvantage that the reaction is not completed on account of the catalytic poison as in Process 1. This process may be represented by the following scheme:

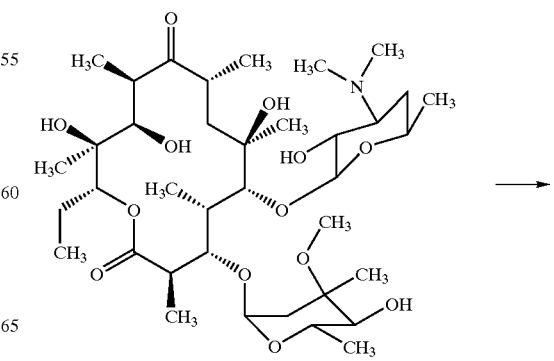

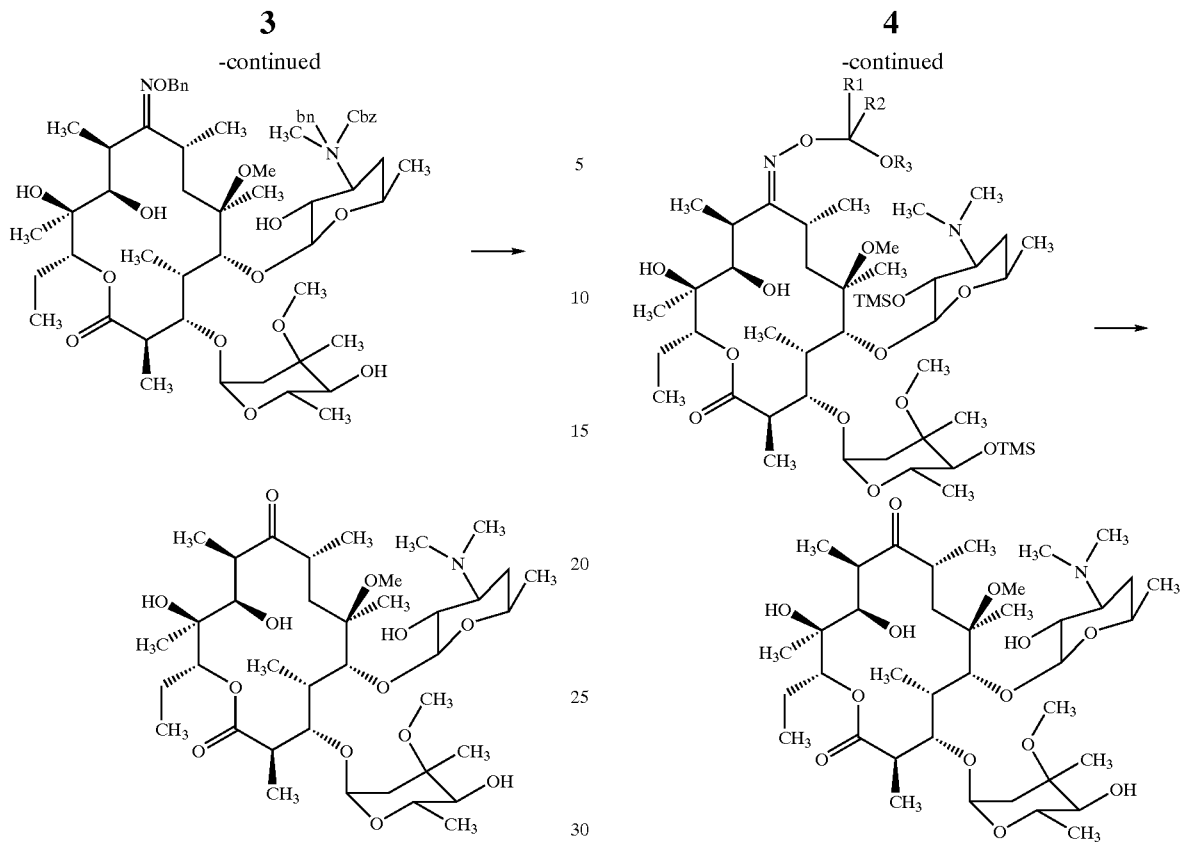

<Process 3>

This process comprises protecting an oxime of erythromycin 9-oxime derivative with a benzyl or ketal derivative, and protecting 2'-OH group and 4'-OH group of said compound with substituted silyl groups, and then methylating a 6-OH group of said compound, and finally deprotecting a protecting group of 9-oxime and trimethylsilyl group of said 2'-O- and 4"-O-groups of said compound simultaneously in a relatively short step to obtain the desired compound.(see Korean Patent Publication Nos. 95-9367 and 96-434). In this case, the 9-oxime derivative used in the trimethylsilylation of 2'-OH and 4'-OH groups should be used in the salt free form. This process is represented by the following scheme:

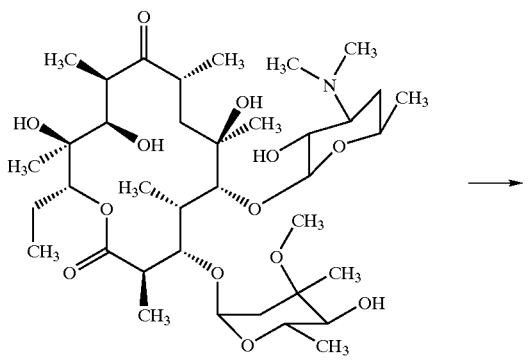

In accordance with the above reaction scheme, the yield of clarithromycin synthesized from an erythromycin A is about 45 to 50%. In the cases where a benzyl derivative is used to protect an oxime for the above reaction schemes, it is difficult to perform such lengthy reactions since the deprotection is carried out by using hydrogen. Another shortcoming is that the ketal derivative, which is used to protect an oxime, has to be used excessively (with about 2 to 3 equivalents) and the total reaction time is rather lengthy. Despite of such shortcoming, the ketal derivative and trimethylsilyl groups can be simultaneously eliminated by an acid treatment.

In efforts to eliminate saprophytic matters that are produced during the 3 synthetic processes mentioned above, a purification step involving precipitation of the synthesized clarithromycin is included in the above processes. However, in most cases, there is about 10 to 20% drop in the yield. In addition, an elimination of saprophytic matters is very difficult if the saprophytic matters having similar characteristics to those of clarithromycin are present.

Accordingly, the inventors have extensively studied a new process for preparing the desired compound in order to solve the above problems of conventional methods and to increase the yield. As a result, it has been found that 1, 3-benzodithiol-2-ylium tetrafluoroborate(BDTF)(Syn. Commun., 471(1976)) represented by the following formula, which is simply synthesized from anthranilic acid, can be used as a protecting group for oxime. The present invention was made possible by means of developing a new and simple process for preparing a high yield of clarithromycin.

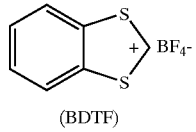

(BDTF)

SUMMARY OF THE INVENTION

It is an object of this invention to provide an erythromycin A 9-O-BDT oxime intermediate represented by the following formula (III), which is useful for the synthesis of clarithromycin prepared by reacting an erythromycin A 9-oxime or hydrochloride thereof with BDTF.

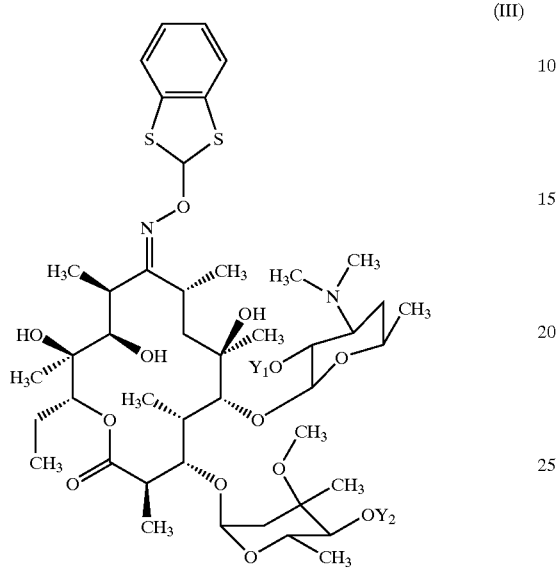

(III)

Wherein, $Y_1$ and $Y_2$ represent hydrogen atoms or trimethylsilyl groups.

Additionally, the present invention provides the compound of the formula (III) ($Y_1$ and $Y_2$ are trimethylsilyl groups) crystallized in the mixed solvent comprising 5 to 10 parts by weight of acetone and 1 to 5 parts by weight of water. The ratio of the compound of said formula (III) and acetone is 2:1.

Furthermore, it is another object of this present invention to provide a process for preparation of clarithromycin, which comprises the steps of:

1) reacting an erythromycin A 9-oxime of the following formula (II) or hydrochloride thereof with 1.0 to 1.2 equivalents of 1, 3-benzodithiol-2-ylium tetrafluoroborate (BDTF) in an aprotic non polar organic solvent in the presence of 1.0 to 2.0 equivalents of pyridine to form an erythromycin A 9-O-BDT oxime derivative of the following formula (III)' having an oxime group which is protected with a benzodithiol(BDT) group, as shown in the following scheme;

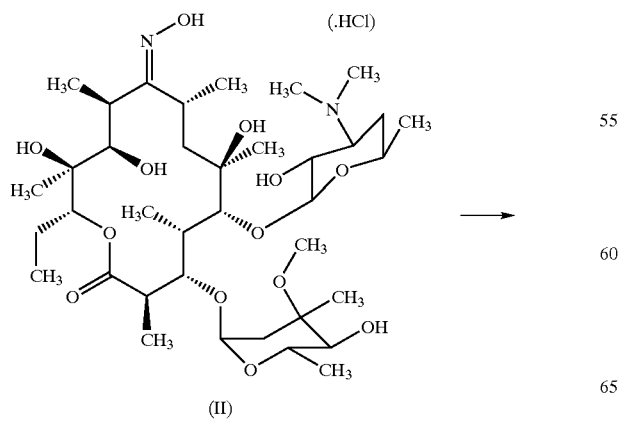

(II)

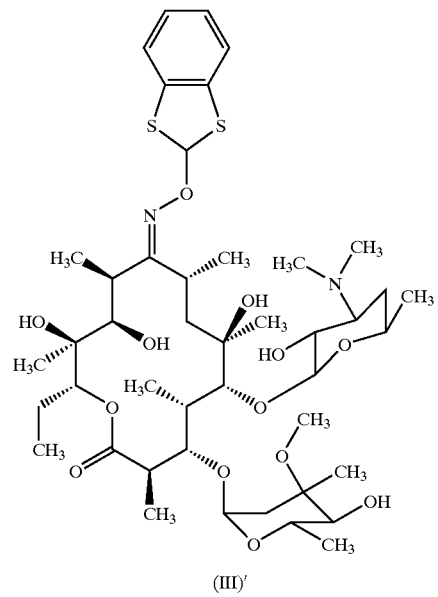

(III)'

2) reacting a compound of formula (III)' synthesized in the above step 1) with 3.0 to 5.0 equivalents of hexamethyldisilazane(HMDS) in the presence of salts such as ammonium chloride, pyridine hydrochloride, pyridine p-toluene sulfonate to form 2'-O,4"-O-bistrimethylsilyl-erythromycin A 9-O-BDT oxime derivative of formula (V), as shown in the following scheme;

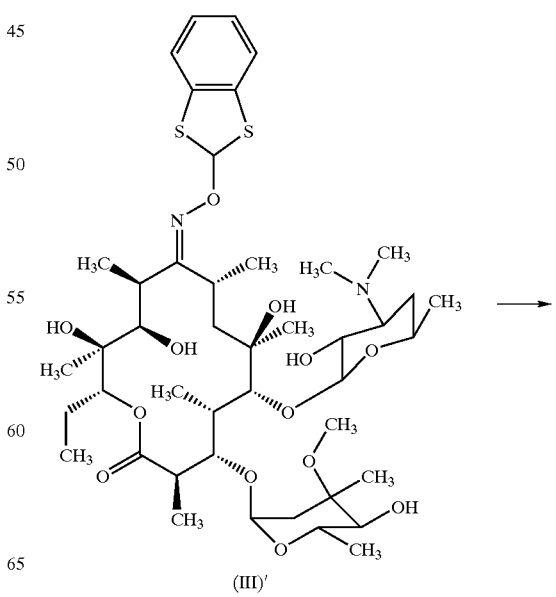

(III)'

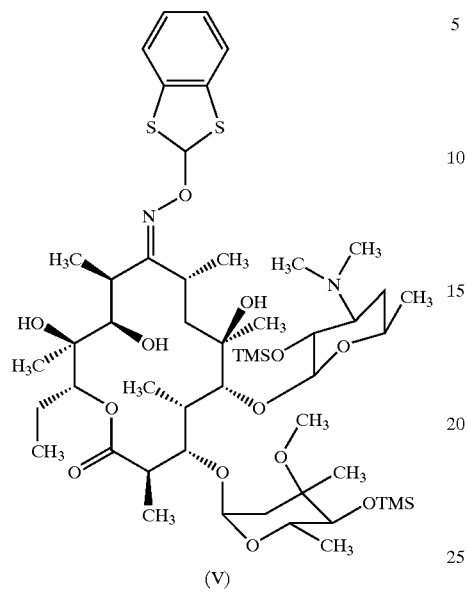

(V)

3) methylating a 6-OH group of the compound of formula (V) synthesized in the above step 2) with 2.0 to 3.0 equivalents of methyl iodide in an aprotic polar solvent in the presence of a strong base to form 2'-O-,4"-O-bistrimethylsilyl-6-O methyl-erythromycin A 9-O-BDT oxime derivative of the following formula (VII) as shown in the following scheme;

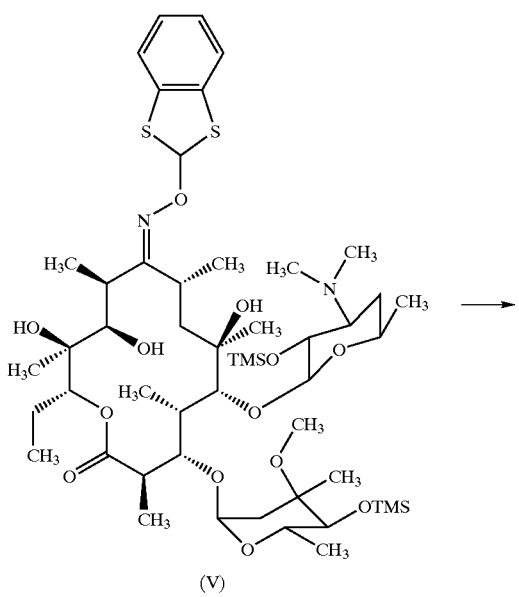

(V)

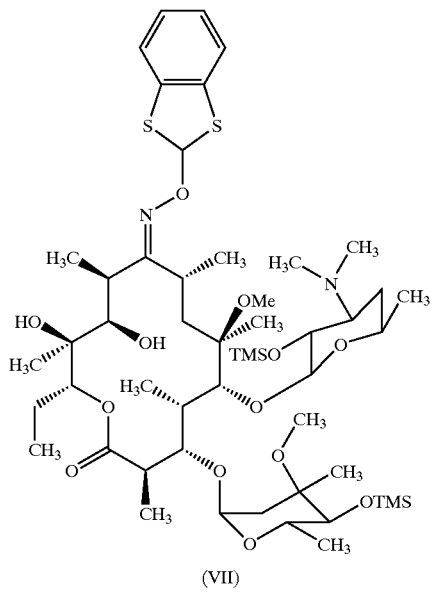

(VII)

4) deprotecting a compound of formula (VII) synthesized in the above step 3) to form the following formula (I).BSDA compound as shown in the following scheme and;

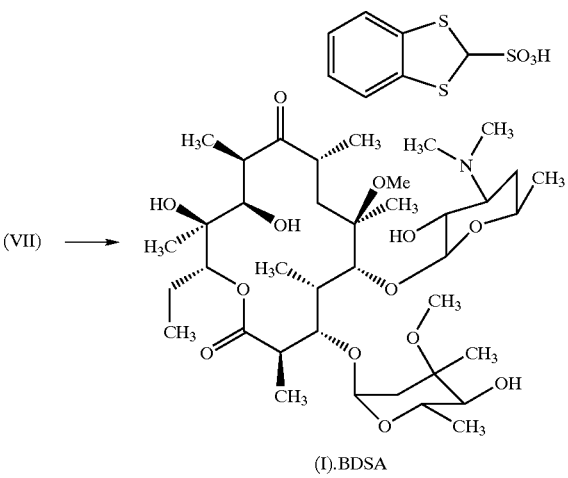

(I).BDSA 5) simply stirring the formula (I).BSDA compound synthesized from the step 4) in water or mixed solvent of water and water-miscible organic solvent in the presence of an inorganic salt or a base, and then filtering it to form the following scheme representing the formula (I):

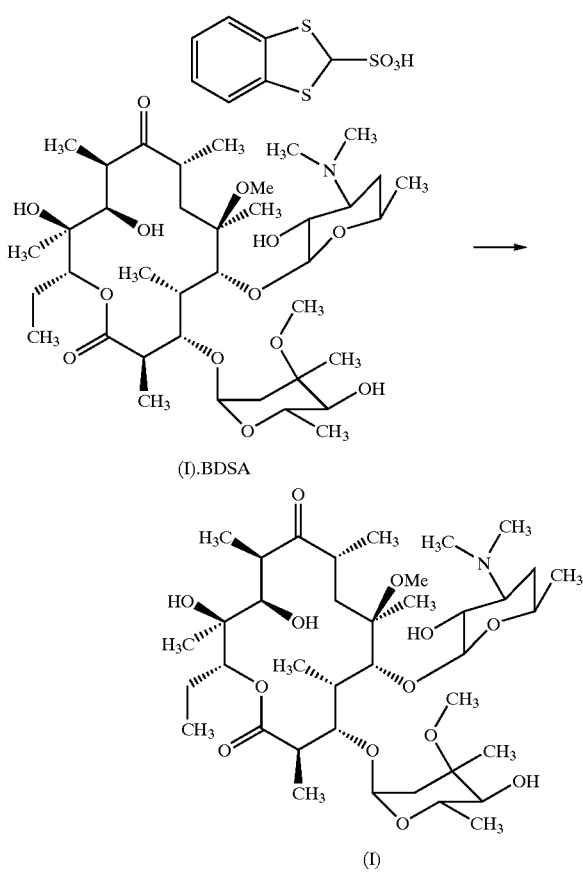

(I).BDSA (I)

DETAILED DESCRIPTION OF THE INVENTION

According to the present invention, step 1 is carried out by reacting an equivalent of erythromycin A 9-oxime representing the above formula (II) or hydrochloride thereof with 1 to 2 equivalents of BDTF in an aprotic nonpolar organic solvent in the presence of 1 to 2 equivalents of pyridine to form erythromycin A-9-O-BDT oxime derivative of the above formula (III)' having an oxime group, which is protected with 1, 3-benzodithiol-2-ylium (BDT) group.

Step 2 is carried out by reacting the resulting compound of the formula (III)' in the above step 1 with 3 to 5 equivalents of hexamethyldisilazane (HMDS) in the presence of salts such as ammonium chloride, pyridine hydrochloride, pyridine p-toluene sulfonate to form 2'-O-, 4"-O-bistrimethylsilyl erythromycin A 9-O-BDT oxime derivative of the above formula (V).

According to the present invention, a methylation of the compound of the above formula (V) at 6-OH group is carried out in an aprotic polar solvent (such as DMSO or DMF), or a mixture ratio of 1:1 of said aprotic polar solvent and THF(tetrahydrofuran), or a mixture ratio of 2:2:0.3 of said aprotic solvent, THF and a non-polar organic solvent (such as isopropylether or t-butylethylether) in an amount of 5 to 10 times that of the compound of the above formula (V) to synthesize the formula (VII). The reaction, which takes about 30 minutes to 2 hours, has to be carried out in the presence of 0 to 2.5 equivalents of $Et_3N$, 1 to 3 equivalents of a strong base such as NaH, alkoxide, KOH and NaOH, and 2 to 3 equivalents of a methylating agent namely methyl iodide at a temperature of −5 to 5° C.

The compound of the above formula (VII) of the present invention is then deprotected by using 1 to 3 equivalents of formic acid ($HCO_2H$) and 4 to 8 equivalents of $NaHSO_3$, $Na_2SO_3$, $Na_2S_2O_4$, or $Na_2S_2O_5$, and ethanol and water ratio of 1:1 in 5 to 10 parts by weight of the mixed solvent of 1:1 of ethanol and water by refluxing with heat for 4 hours. As a result, 1, 3-benzodithiole-2-sulfonic acid (BDSA) of clarithromycin representing the above formula (I) is synthesized.

BDSA, which is synthesized by reacting a protective group, BDT, with a deoximizing agent such as $NaHSO_3$, $Na_2SO_3$, $Na_2S_2O_4$, or $Na_2S_2O_5$ in the presence of HCOOH, forms into its salt form, represented as the above formula (I).BDSA when joined with a 3'-N,N-dimethylamino group. After the reaction is completed and the temperature is lowered to room temperature, the desired compound, which is crystallized in the reaction solvent, is then purified. As a result, the separation of the desired compound from the other by-products becomes very feasible. In this case, since the reaction between a BDT group and a deoximizing agent occurs first in the order of deprotection, oxime is synthesized without having any protection. Clarithromycin is synthesized as a result of a deoximization and an elimination of trimethlysilyl group in the final step.

According to a process of the present invention, the above formula (I).BDSA is reacted with an inorganic salt such as $K_2CO_3$, $Na_2CO_3$, or KOH to remove BDSA in a neutralizing reaction and finally a pure crystal form of clarithromycin representing the above formula (I) is obtained.

It is yet another object of this invention to provide another process for the preparation of clarithromycin of formula (I) by adding hexamethyldisilazane (HMDS) to erythromycin A 9-oxime representing the formula (II) or hydrochloride thereof to form 2'-O,4"-O-bistrimethylsilyl-erythromycin A 9-oxime derivative of formula (IV) in place of the above step 1), and reacting 2'-O-,4"-O-bistrimethylsilyl-erythromycin A 9-oxime derivative of formula (IV) in an aprotic organic solvent such as MC in the presence of pyridine with 1 to 2 equivalents of BDTF to form a quantitative yield of 2'-O-, 4"-O-bistrimethylsiliyl-erythromycine A 9-O-BDT oxime derivative of formula (V) in place of the above step 2), as shown in the following scheme;

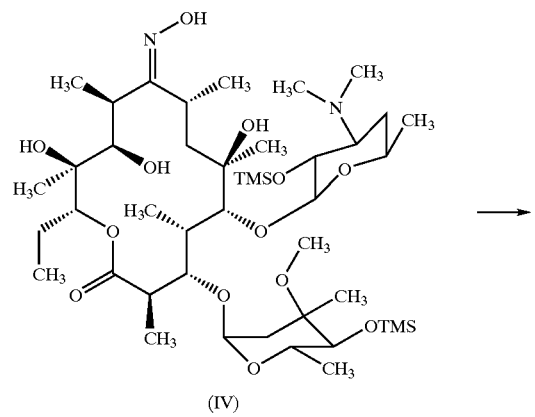

(IV)

-continued

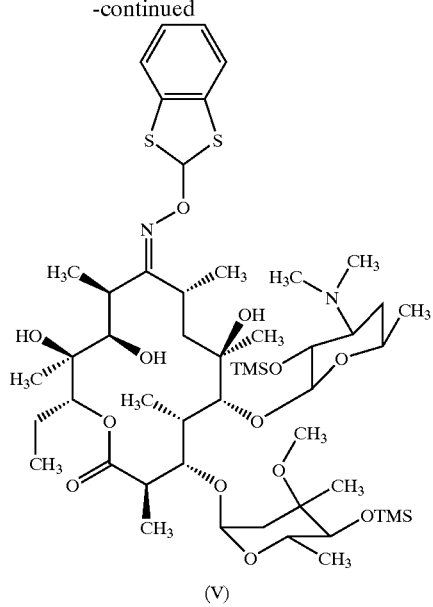

(V)

Once the compound of the above formula (V) is mixed and dissolved in a mixed solvent of 1 to 5 parts by weight of water and 5 to 10 parts by weight of acetone (preferably in the mixture ratio of 3:10) to form a crystalline solvate comprising the compound of the above formula (V) and acetone in 2:1 ratio.

The following are examples to illustrate the present invention in further detail but they do not limit the scope of the invention in anyway.

EXAMPLE 1

(1) Preparation of 2'-O,4"-O-bistrimethylsilylerythromycin A 9-Oxime 157 g(0.2 mole) of erythromycin A 9-oxime.HCl and 5.4 g(0.1 mole) of ammonium chloride were placed into a 2 l flask, and 600 ml of dimethylformamide were added thereto. 217 ml(1 mole) of hexamethyldisilazane (HMDS) were slowly added to the mixture, and then stirred at a temperature of 35 to 40° C. for 3 hours. 30 ml of water were added to the mixture, and then stirred for one hour. Thereafter, 600 ml of water were further added thereto. After further stirring the mixture for 30 minutes, 150 ml of 2N-NaOH were added thereto, and the mixture was then extracted with 600 ml of dichloromethane. An aqueous solution layer was again extracted with 2 l of dichloromethane. After the organic layers were combined, the mixture was washed with 200 ml of saturated saline, solution, and then dehydrated with anhydrous $MgSO_4$. The solvent was removed under reduced pressure to obtain 170.5 g of the title compound as a foam(yield 95.4%).

1H NMR($CDCl_3$) δ 0.16(s,9H, -OTMS), 0.19(s,9H, -OTMS)

(2a) Preparation of 2'-O-,4"-O-bistrimethylsilyl-erythromycin A 9-O-BDT Oxime 8.93 g(10 mmole) of 2'-O-,4"-O-bistrimethylsilyl-erythromycin A 9-oxime prepared in the above 1) were dissolved in 40 ml of dichloromethane, and 2.52 g(1.05 mmole) of BDTF were then added thereto at a temperature of 20 to 25° C. 1.13 ml(14 mmole) of pyridine were slowly added to the mixture, and then stirred for 30 mins. 50 ml of methylene dichloride and 50 ml of water were added to the mixture, and then extracted. The organic layer was washed with saturated saline solution, dehydrated with anhydrous $MgSO_4$, filtered, and then dried to obtain 10.25 g of the title compound as a foam(yield 98.0%).

1H NMR($CDCl_3$) δ 7.37(m,2H), 7.11(m,2H), 6.88(s,1H), 3.28(s,3H), 2.63(s,6H), 0.16(s,18H)

(2b) Preparation of 2'-O-,4"-O-bistrimethylsilylerythromycin A 9-O-BDT Solvate with Oxime and Acetone Ratio of 2:1

30.75 ml of water was slowly added to the desired compound of the above in the form of a foam that has already been dissolved in 102.5 ml of acetone. The resulting solid is then placed in an ice bath, stirred for an hour, filtered and dried. As a result, 2"-O-,"4-O-bistrimethylsilyl-erythromycin A 9-O-BDT oxime 8.95 g(85.0% yield) of solvate with oxime and acetone ratio of 2:1 was obtained.

$^1$H-NMR($CDCl_3$) δ 7.37(m,2H), 7.11(m,2H), 6.88(s,mH), 3.28(s,3H), 2.63(s,6H), 2.10(s,6H), 0.16(s,18H)

(3) Preparation of 2'-O-,4"-O-bistrimethylsilyl-6-O-methyl-erythromycin A 9-O-BDT Oxime Before adding 10.45 g(10 mmole) of 2'-O,4"-O-bistrimethylsilyl-erythromycin A 9-O-BDT oxime prepared in the above 2) to 160 ml of mixture of anhydrous THF, anhydrous DMSO and t-butylmethylether(2:2:0.3). 1.39 ml of $Et_3N$ was added to the mixture. The temperature was adjusted to 0° C. At this point, 0.98 g(15 mmole) of KOH and 1.25 ml(20 mmole) of methyl iodide were added thereto. The reaction was completed after stirring the mixture for an hour. Thereafter, the mixture was sequentially extracted with 100 ml of hexane and 100 ml of water. The organic layer was washed with about 10% saline solution, dehydrated with anhydrous $MgSO_4$, and then filtered. The solvent was removed under reduced pressure to obtain 10.46 g of the desired compound in the form of a foam(yield 98.8%).

1H NMR($CDCl_3$) δ 7.05~7.40(m,4H), 6.89 (s,1H), 3.31 (s,3H), 2.63(s,3H), 2.22(s,6H), 0.17(s,9H), 0.09(s,9H)

(4) Preparation of 1, 3-Benzodithiol-2-sulfonic Acid Salt 10.60 g(10 mmole) of 2'-O-,4"-O-bistrimethylsilyl-6-O-methyl-erythromycin A 9-O-BDT oxime prepared in the above 3) were dissolved in 50 ml of ethanol, and 50 ml of water were then added thereto. 0.57 ml(15 mmole) of formic acid and 4.16 g(40 mmole) of sodium hydrogen sulfate ($NaHSO_3$) were added to the mixture, and then refluxed with heat for 2 hours. 0.19 ml(0.5 mmole) of formic acid was added additionally to the reaction mixture and refluxed again with heat for another 2 hours. After the reaction was completed, the temperature of the reaction mixture was lowered to room temperature. The resulting solid was filtered and dried to obtain 5.80 g(59.1% yield) of the desired compound.

$^1$H NMR($CDCl_3$+DMSO-$d_6$) δ 7.18(m,2H), 7.01(m,2H), 5.61(s,1H), 5.05(d,1H), 4.89(d,1H), 4.55(d,1H), 3.97(m, 2H), 3.70(m,5H), 3.40(m,2H), 3.32(s,3H), 3.02(s,8H), 2.83 (dd,6H), 2.59(m,1H), 2.34(d,1H), 1.40~1.95(m,6H), 1.37(s, 3H), 1.10~1.35(m,26H), 0.85(t,3H)

(5) Preparation of Clarithromycin 9.82 g(10 mmole) of the resulting compound from the above step 4 was added to 19.64 ml of ethanol and 49.1 ml of water and stirred. 2.76 g of $K_2CO_3$ dissolved in 49.1 ml of water was slowly added to the mixture thereto. The resulting crystal, which was then placed in 14 mg of $K_2CO_3$ dissolved in 98.2 ml of water and stirred for 5 minutes, was filtered and dried to obtain 7.14 g(95.5% yield) of the desired compound.

$^1$H-NMR(CDCl$_3$) δ 5.08(d,1H), 4.93(d,1H), 4.44(d,1H), 4.02(m,1H), 3.99(s,1H), 3.78(m,2H), 3.67(d,1H), 3.33~3.46 (m,2H), 3.34(s,3H), 3.19(t,2H), 3.06(s,3H), 2.89~3.02(m, 2H), 2.89(m,1H), 2.58(m,1H), 2.40(m,2H), 2.29(s,6H), 1.93 (d,1H), 1.40~1.95(m,6H), 1.42(s,3H), 1.10~1.35(m,26H), 0.85(t,3H)

EXAMPLE 2

10.33 g(97.5% yield) of 2'-O-,4"-O-bistrimethylsilylerythromycin A 9-O-BDT oxime compound was obtained by the same method as in Example 1 except for 0.8 g(20 mmole) of 60% NaH used in the place of KOH in the step (3) of the above Example 1.

EXAMPLE 3

7.49 g(10 mmole) of erythromycin A 9-oxime were dissolved in 40 ml of methylene dichloride, and 1.13 ml(14 mmole) of pyridine were added thereto. 2.64 g(11 mmole) of BDTF was added portion-wise to the mixture at room temperature, and then stirred at the same temperature for 30 minutes. After the reaction was completed, 40 ml of methylene dichloride and 60 ml of water were added to the mixture, and then extracted. The organic layer was washed with 10% saline solution, dehydrated with anhydrous $MgSO_4$, and then filtered. The solvent was removed under reduced pressure to obtain 8.76 g of the desired compound in the form of a foam(yield 97.2%). The rest of the procedure was performed in the same manner as in the step (2) of the above Example 1.

1H NMR(CDCl$_3$) δ 7.30(m,2H), 7.13(m,2H), 6.87(s,4H), 3.30(s,3H), 2.50(s,6H)

EXAMPLE 4

9.01 g(10 mmole) of A 9-O-BDT oxime prepared in the step (2) of the above Example 1 and Example 3 and 0.8 g(15 mmole) of ammonium chloride were added to 27 ml of dimethylformamide. 8.44 ml (40 mmole) of hexamethyldisilazane(HMDS) were slowly added to the mixture, and then stirred at a temperature of 40 to 50° C. for 5 hours. The mixture was sequentially extracted with 60 ml of water and 60 ml of dichloromethane, and the aqueous layer was again extracted with 20 ml of dichloromethane. The organic layers were combined, washed with 20 ml of saturated saline solution, and then dehydrated with anhydrous $MgSO_4$. The solvent was removed under reduced pressure to obtain 9.53 g of the desired compound in the form of foam (yield 91.2%). The rest of the procedure was performed in the same manner as in the step (3) of the above Example 1.

EXAMPLE 5

5.67 g(57.7% yield) of 1, 3-benzodithiol-2-sulfonic acid was obtained by the same method as in Example 1 except that 8.2 g(40 mmole) of $Na_2S_2O_4$ used in the place of $NaHSO_3$ in the step (4) of the above Example 1.

EXAMPLE 6

5.49 g(55.9% yield) of 1, 3-benzodithiol-2-sulfonic acid was obtained by the same method as in Example 1 except that 7.84 g(40 mmole) of $Na_2S_2O_5$ used in the place of $NaHSO_3$ in the step (4) of the above Example 1.

EXAMPLE 7

5.62 g(57.2% yield) of 1, 3-benzodithiol-2-sulfonic acid was obtained by the same method as in Example 1 except that 5.04 g(40 mmole) of $Na_2SO_3$ used in the place of $NaHSO_3$ in the step (4) of the above Example 1.

The following are the effects of this present invention:

First of all, in the prior art, the use of benzyl derivative as a protecting group of oxime makes the process difficult since the deprotection should be carried out by the hydrogenation reaction using the catalyst, and this deprotection is not completed on account of the catalytic poison. Furthermore, in case where the ketal derivative is used as a protecting group of oxime during the deprotection, it has the advantage that a trimethylsilyl group and an oxime may be simultaneously deprotected. However, it also has some disadvantages such as an excessive use of ketal derivative and an extended reaction time. However, according to the present invention, the protection of an oxime may easily be carried out in near quantitative manner by using 1,3-benzodithiol-2-ylium tetrafluoroborate (BDTF) which is simply synthesized from anthranilic acid. Furthermore, since the said BDTF group used as a protecting group of oxime may be simultaneously removed together with trimethylsilyl group and oxime group when the deprotection is carried out under acidic conditions, it simplifies the process, and it is thus possible to obtain about 52% yield of the desired compound of formula (I) by performing this short process involving erythromycin A.

Secondly, in the prior art, since a step involving crystallization in ethanol was necessary after the deprotection for the purification of the purest form of clarithromycin, about 10 to 20% drop in the yield has incurred as a result. However, in the present invention, the formation of the salts by joining the resulting clarithromycin from the deprotection and the resulting BDSA from the reaction between a protective group and a deoximizing agent is carried out and cooled at room temperature for an immediate crystallization of the salts in the reaction mixture for a separation of a purest form of crystals.

Consequently, once the salts are eliminated by neutralization, clarithromycin having a high purity and yield can be obtained and the purification step can be significantly simplified.

Thirdly, while a protective group of oxime in the prior art has only protected oxime and allowed a selectivity for introduction of a methyl group, a BDTF group that has been used in this present invention is responsible for not only protecting oxime and allowing the selectivity, but also forming a BDSA group by reacting with deoximizing agent such as $NaHSO_3$, $Na_2SO_3$, $Na_2S_2O_4$ and $Na_2S_2O_5$ and forming clarithromycin salt that can immediately be extracted from the reaction mixture as crystals to effectively indicate that the purification step can be significantly simplified.

What is claimed is:

1. An erythromycin A 9-O-benzodithiol oxime intermediate represented by the following formula (III) useful for synthesis of clarthromycin and crystalline solvate thereof;

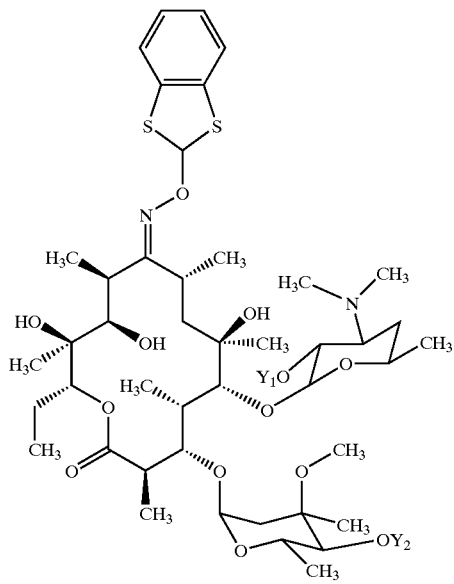

(III)

wherein, $Y_1$ and $Y_2$ are independently a hydrogen atom or trimethylsilyl group.

2. The intermediate compound and crystalline solvate thereof according to claim 1, wherein said crystalline solvate consists of said intermediate compound of formula (III), in which $Y_1$ and $Y_2$ are trimethylsilyl groups, and acetone in the ratio of 2 to 1.

3. A process for the preparation of clarithromycin of formula (I), which comprises the steps of:

1) reacting an erythromycin A 9-oxime of the following formula (II) or hydrochloride thereof with 1.0 to 1.2 equivalents of 1,3-benzodithiol-2-ylium tetrafluoroborate (BDTF) in an aprotic non polar organic solvent in the presence of 1.0 to 2.0 equivalents of pyridine to synthesize an erythromycin A 9-O-BDT oxime derivative of formula (III)' having an oxime group which is protected with 1,3-benzodithiol (BDT) group;

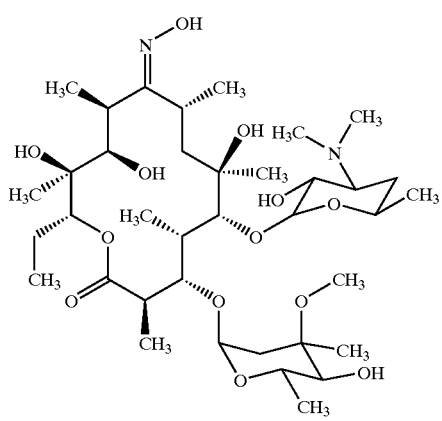

(II)

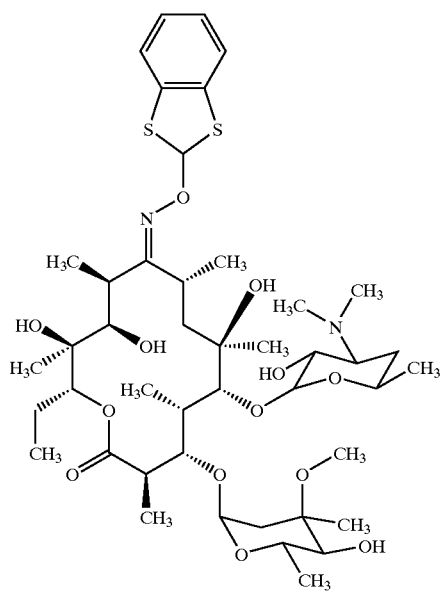

(III)'

2) reacting a compound of formula (III)' synthesized in the step 1) with 3.0 to 5.0 equivalents of hexamethyldisilazane (HMDS) in the presence of salts selected from the group consisting of ammonium chloride, pyridine hydrochloride, and pyridine p-toluene sulfonate to form 2'-O-,4"-O-bistrimethylsilylerythromycin A 9-O-BDT oxime derivative of formula (V);

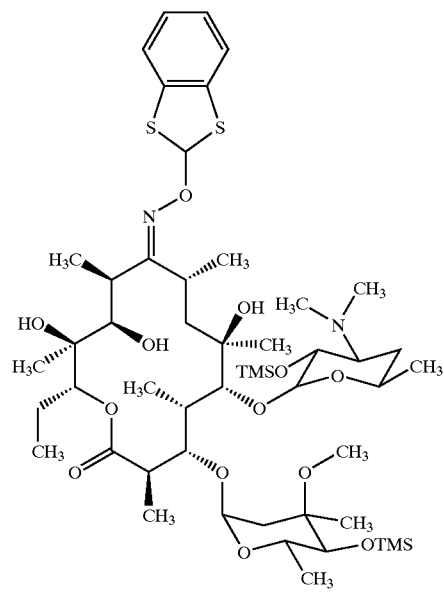

(V)

3) methylating a 6-OH group of the compound of formula (V) synthesized in the step 2) with methyl iodide in a solvent in the presence of strong base to form 2'-O-, 4"-O-bistrimethylsilyl-6-O-methyl-erythromycin A 9-O-BDT oxime derivative of formula (VII);

(VII)

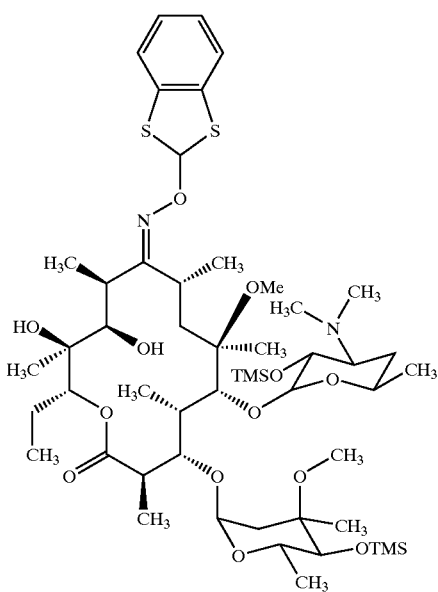

4) deprotecting the compound of formula (VII) synthesized in the step 3) to form the following formula (I).BDSA; and

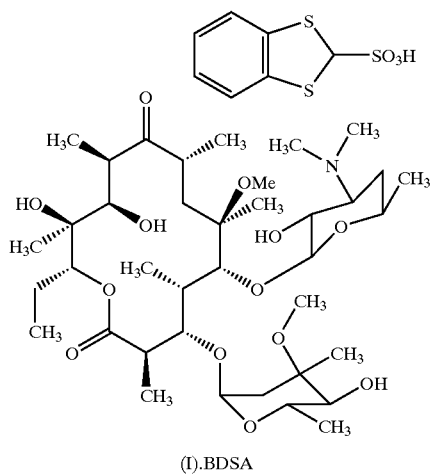

(I).BDSA 5) stirring the compound of formula (I).BDSA synthesized in the step 4) in water or a mixture of water and water-miscible organic solvent in the presence of an inorganic salt or a base and then filtering it to form a clarithromycin representing the following formula (I)

(I)

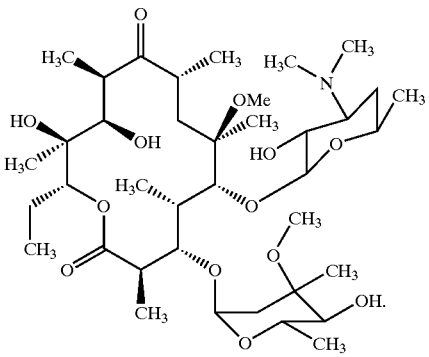

4. The process according to claim 3, wherein said solvent used in the step 3) is selected from an aprotic polar solvent selected from DMF or DMSO, a mixture of said aprotic polar solvent and THF (1:1), or a mixture of said aprotic polar solvent, THF, and a non-polar organic solvent selected from isopropylether or t-butylmethylether (2:2:0.3), and the methylation of the compound of formula (V) in the step 3) is carried out at a reaction temperature of −5 to 5° C. for 30 minutes to 2 hours with 2.0 to 3.0 equivalents of methyl iodide as a methylating agent under said solvent in an amount of 5 to 10 times of the compound of formula (V) and 1.0 to 3.0 equivalents of a strong base selected from the group consisting of KOH, alkoxide and NaH in the presence of 0 to 2.5 equivalents of $Et_3N$.

5. The process according to claim 3, wherein the water-miscible organic solvent in the step 5) is ethanol.

6. The process according to claim 3, wherein the deprotection of the step 4) is carried out by using 1.0 to 3.0 equivalents of formic acid and 4.0 to 8.0 equivalents of $NaHSO_3$, $Na_2S_2O_4$, $Na_2S_2O_5$ or $Na_2SO_3$ in 5 to 10 parts by weight of the mixture ratio of 1:1 of ethanol and water, and cooled at room temperature before being crystallized.

7. The process according to claim 3, wherein the neutralizing reaction of the step 5) is carried out by preparing the solution of the compound of the formula (I). BDSA by mixing one part by weight of said compound and 10 to 20 parts by weight of ethanol in a mixture ratio of 1:1, and adding 3 to 5 parts by weight of the solvent which includes 1 to 2 parts by weight of an inorganic salt or base to said solution.

8. A process for the preparation of clarithromycin of the following formula (I), which comprises the steps of:

1) adding hexamethyldisilazane (HMDS) to erythromycin A 9-oxime or hydrochloride thereof to form 2'-O-4"-O-bistrimethylsilyl-erythromycin A 9-oxime derivative of the following formula (IV);

(IV)

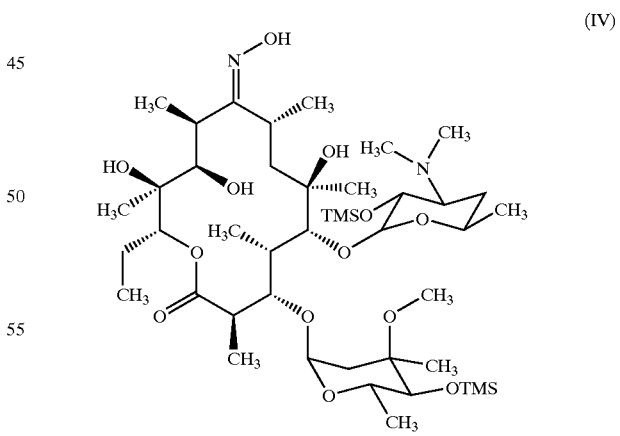

2) reacting 2'-O'-4"-O-bistrimethylsilyl-erythromycin A 9-oxime derivative of formula (IV) in an aprotic organic solvent in the presence of pyridine with a BDTF to form 2'-O'-4"-O-bistrimethylsilyl-erythromycin A 9-O-BDT oxime derivative of the following formula (V);

(V)

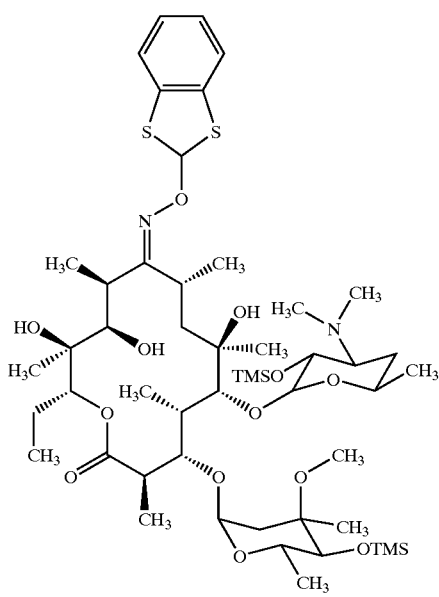

3) methylating a 6-OH group of the compound of formula (V) synthesized in the step 2) with methyl iodide in an aprotic polar solvent in the presence of strong base to form 2'-O-,4"-O-bistrimethylsilyl-6-O-methyl-erythromycin A 9-O-BDT oxime derivative of the following formula (V);

(VII)

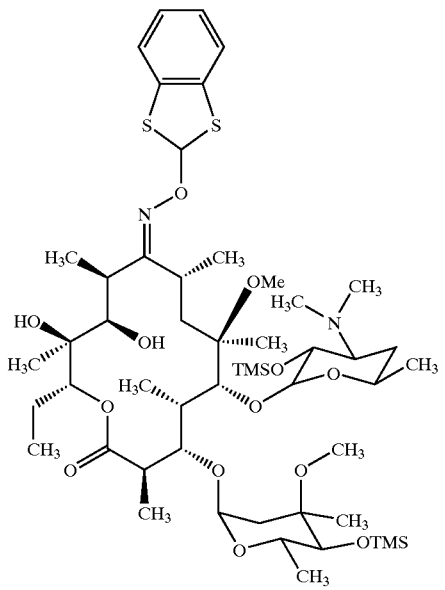

4) deprotecting the compound of formula (VII) synthesized in the step 3) to form the following formula (I). BDSA; and

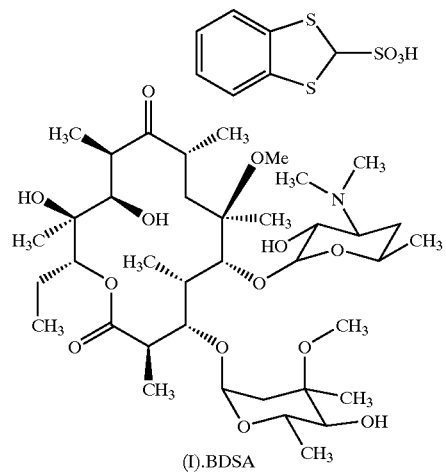

(I).BDSA 5) stirring the compound of formula (I). BDSA synthesized in the step 4) in water or a mixture of water and water-miscible organic solvent in the presence of an inorganic salt or a base and then filtering it to form a clarithromycin representing the following formula (I)

(I)

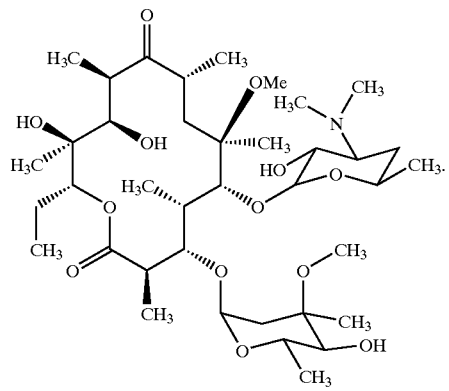

* * * * *

UNITED STATES PATENT AND TRADEMARK OFFICE
CERTIFICATE OF CORRECTION

PATENT NO. : 6,600,025 B1
DATED : July 29, 2003
INVENTOR(S) : Tae Suk Lee et al.

It is certified that error appears in the above-identified patent and that said Letters Patent is hereby corrected as shown below:

Column 13,
Line 37, "4H" should read -- 1H --

Column 18,
Line 31, between the word "by weight of" and "ethanol" the following should be added: -- water or 5 to 10 parts by weight of water and 5 to 10 parts by weight of --

Column 19,
Line 26, "(V)" should read -- (VII) --

Signed and Sealed this

Eighteenth Day of January, 2005

JON W. DUDAS
*Director of the United States Patent and Trademark Office*